US006998074B1

(12) United States Patent
Radulescu

(10) Patent No.: US 6,998,074 B1
(45) Date of Patent: Feb. 14, 2006

(54) METHOD FOR FORMING POLYMER MICROSPHERES

(75) Inventor: Delia Radulescu, Plano, TX (US)

(73) Assignee: MicroFab Technologies, Inc., Plano, TX (US)

( * ) Notice: Subject to any disclaimer, the term of this patent is extended or adjusted under 35 U.S.C. 154(b) by 260 days.

(21) Appl. No.: 10/643,913

(22) Filed: Aug. 20, 2003

Related U.S. Application Data

(60) Provisional application No. 60/406,731, filed on Aug. 30, 2002.

(51) Int. Cl.
*B29B 9/00* (2006.01)
*A61K 9/14* (2006.01)
*B41J 2/045* (2006.01)

(52) U.S. Cl. .................. 264/14; 264/4.1; 264/4.33; 264/5; 424/489; 347/20; 347/68

(58) Field of Classification Search ............... 264/4.1, 264/4.33, 5, 14; 424/489; 347/20, 68
See application file for complete search history.

(56) References Cited

U.S. PATENT DOCUMENTS

| 4,138,383 | A | 2/1979 | Rembaum et al. |
| 4,444,961 | A | 4/1984 | Timm |
| 4,956,128 | A | 9/1990 | Hommel et al. |
| 4,981,625 | A | 1/1991 | Rhim et al. |
| 5,053,100 | A | 10/1991 | Hayes et al. |
| 5,260,002 | A | 11/1993 | Wang |
| 5,376,347 | A | 12/1994 | Ipponmatsu et al. |
| 5,643,506 | A | 7/1997 | Rourke |
| 5,736,074 | A | 4/1998 | Hayes et al. |
| 6,224,794 | B1 | 5/2001 | Amsden et al. |
| 6,277,413 | B1 | 8/2001 | Sankaram |
| 6,331,317 | B1 | 12/2001 | Lyons et al. |
| 6,367,925 | B1 | 4/2002 | Chen et al. |
| 6,513,894 | B1 * | 2/2003 | Chen et al. .................. 347/11 |
| 6,527,357 | B1 * | 3/2003 | Sharma et al. ............... 347/17 |

OTHER PUBLICATIONS

K. J. Pekarek, M. J. Dyrud, K. Ferrer, Y. S. Jong, E. Mathiowitz, "In Vitro and in Vivo Degradation of Double-Walled Polymer Microspheres," Journal of Controlled Release, No. 40, p. 169-178, (1996).
C. Berkland, K. Kim, D. W. Pack, "Fabrication of PLG Microspheres with Precisely Controlled and Monodisperse Size Distributions," Journal of Controlled Release, No. 73, p. 59-74, (2001).
Danesi, Innocenti, Fogli, Gennari, Baldini, DiPaolo, Salvadori, Bocci, Conte, Deltacca, "Pharmacokinetics and Pharmacodynamics of Combination Chemotherapy with Paclitaxel and Epirubicin in Breast Cancer Patients," Journal of Clinical Pharmacol, No. 53, p. 508-518, (2002).
Sousa-Escandon, Vazquez, Quintero-Aldana, Picallo, Neira, Garcia-Novio, Mateo, Rico, Mel, "Neo-Adjuvant Treatment of Infiltrating Transitional-Cell Carcinoma of the Bladder with Paclitaxel and Cisplatin: A Phase II Trial," International Journal of Urology, No. 9, p. 162-166, (2002).

* cited by examiner

Primary Examiner—Samuel A. Acquah
(74) Attorney, Agent, or Firm—Locke Liddell & Sapp LLP

(57) ABSTRACT

A method for forming polymer microspheres includes dispensing polymeric material from an orifice of a drop-on-demand ink jet printhead while the orifice is immersed in a solvent extraction media.

5 Claims, 1 Drawing Sheet

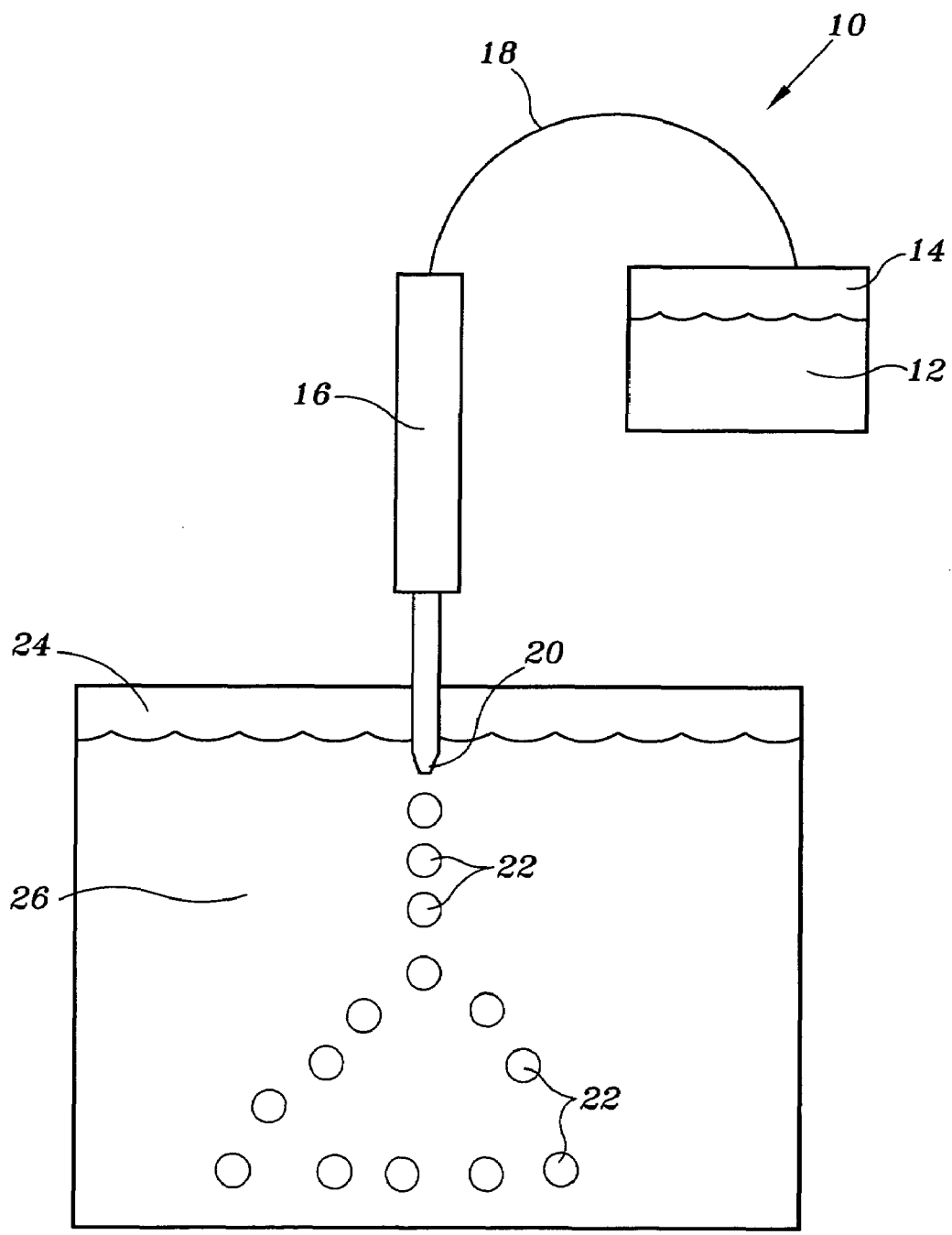

METHOD FOR FORMING POLYMER MICROSPHERES

CROSS-REFERENCE TO RELATED APPLICATION

This application claims the benefit of U.S. Provisional Application Ser. No. 60/406,731 filed Aug. 30, 2002 and entitled, "Precision Polymer Microspheres Produced by Ink Jet Technology".

STATEMENT REGARDING FEDERAL SPONSORED RESEARCH AND DEVELOPMENT

This invention was made with government support under contract DMI-0109462 awarded by the National Science Foundation. The United States government may have certain rights in this invention.

TECHNICAL FIELD OF THE INVENTION

The present invention relates to methods for manufacturing uniformly-sized polymer microspheres using ink jet technology, and more specifically to a method in which jetting is performed with drop-on-demand piezoelectric device having an orifice immersed in an extraction media.

BACKGROUND OF THE INVENTION

When active substances are encapsulated in drug delivery systems, their bioavailability and therapeutic index is improved over an extended period of time. A drug delivery system including polymer microspheres has been developed for injection, implants, transdermal patches, and aerosols. Polymeric microspheres have a variety of uses in the medical and industrial areas since they provide a large surface area, can be easily injected, and do not require removal after completion of drug release.

Method for producing microspheres include single and double emulsion solvent evaporation, spray drying, phase separation, simple and complex coacervation, and interfacial polymerization. However, most methods generate microspheres having a wide size distribution with little or no control over the average diameter. Control of sphere size and size distribution are the ultimate goals of drug delivery. A particular release rate and a desired route of administration typically require a particular sphere size. Using filters is a possibility, but the use of filter results in a waste of expensive material. Therefore, several methods that allow control over particle size and size distribution have been proposed. Each of these methods has drawbacks that prevent the use of microspheres in various application.

Proposed methods include high shear emulsification which generates microspheres of average diameter not higher than 25 $\mu$m but many application require a greater size. This method also applies temperature restrictions on the solutions that can be used. Thus, the method cannot be used for polymers with low melting temperature, like many polylactide-co-glycolides (PLGAs) or for encapsulating temperature-sensitive drugs, like proteins.

Monomer polymerization techniques are not appropriate for drug encapsulation due to harsh chemical and/or physical environments that can denaturate drugs. In addition, some of these methods lead to formation of microspheres with diameters not grater than 3.5 $\mu$m.

An electrostatically controlled extrusion method is not capable of generating uniformly-sized microspheres.

In a porous membrane method, only low viscosity polymers can be used. Even if the polymer solution is of low viscosity, addition of a drug can increase the overall viscosity, thus limiting not just the range/concentrations of the polymers that can be used, but also the drug loading concentrations.

Injection methods do not demonstrate control over average diameter through manipulation of process parameters. Moreover, such methods have the disadvantage of not being able to produce microspheres of narrow size distributions.

A vibratory excitation process is based on continuous mode jetting in which a flow of polymer exits a piezoelectric orifice and a small perturbation applied to the flow breaks the jet into small drops. This method requires low voltages and high frequencies to be applied to the piezoelectric (PZT) device, as well as significant pressure to the polymer solution. Under this pressure, only high quantities of expensive fluid can be jetted.

A need has thus arisen for a simple and controllable manufacturing method for forming uniformly-sized polymer microspheres.

SUMMARY OF THE INVENTION

A method for forming polymer microspheres includes dispensing polymeric material from an orifice of a drop-on-demand ink jet printhead while the orifice is immersed in a solvent extraction media.

BRIEF DESCRIPTION OF THE DRAWING

For a more complete understanding of the present invention and for further advantages thereof, reference is now made to the following Description of the Preferred Embodiments taken in conjunction with the accompanying Drawing which is a block diagram of a system for forming polymer microspheres in accordance with the present invention.

DESCRIPTION OF THE PREFERRED EMBODIMENTS

The FIGURE illustrates an ink-jet printing system, generally identified by the numeral 10 for forming polymer microspheres in accordance with the present invention. A biodegradable polymer solution 12 to be jetted is dissolved in a suitable solvent and is loaded into a reservoir 14 of an ink-jet printhead 16. Reservoir 14 and printhead 16 are connected through tubing 18. Ink-jet printhead 16 includes a glass tube bonded to piezoelectric materials that creates a sonic waveform when stimulated by a computer-generated waveform. The electrical stimulation causes displacement of the piezoelectric materials that initiates a sonic pressure wave within the glass tube that drives material out of an orifice 20. The orifice 20 is the distal, polished portion of the glass tube where materials form microspheres or drops 22 that are expelled form the ink-jet printhead 16 in a drop-on-demand mode. Ink-jet printing devices are shown and described in U.S. Pat. No. 5,053,100 to Hayes et al. and U.S. Pat. No. 6,367,925 to Hayes et al. which disclosures and drawings are hereby incorporated by reference.

Printhead 16 is controlled by a wave function generating software and appropriate electronics. When initiated, printhead 16 will deliver drops 22 of polymer solution 12 from reservoir 14 into a reservoir 24 containing a suitable solvent extraction media 26.

Orifice 20 of printhead 16 is immersed within media 26 so that drops 22 of polymer solution 12 are dispersed direction into media 26.

Polymers included within solution 12 include, for example, Synthetic Bioabsorbable Polymers: 1. Polyesters and Polylactones (examples polylactide, poly-L-lactide, poly-D-lcatide, poly-D,L-lactide, polyglycolide, polylactide-glycolide, poly-L-lactide-glycolide, poly-D-lactide-glycolide, poly-D,L-lactide-glycolide, poly-p-dioxanone, copolymers of -p-dioxanone with L-lactide, D-lactide, D,L-lactide, glycolide all combinations, copolymers of 6-caprolactone, and/or 3-oxacaprolactone, and/or trimethylene carbonate and/or 1,5-dioxepan-2-one with L-lactide, and/or D-lactide, and/or D,L-lactide, and or glycolide, and/or p-dioxanone. It is to be understood that all useful polyesters and polylactones are not limited to these examples; 2. Polyalkylene oxalate such as isomorphic copoyoxalats of cyclic and alicyclic diols such as cyclohexane dimethylol, and other polymers including polyalkylene oxamates, and others; 3. Block copolyesters: such a polyethyleneglycol-polylactide, or -polyglycolide, or -polylactide/glycolide, polyethyelene-p-phenylenediglycol-polylactide, or -polyglycolide, or -polylactide/glycolide, or -poly-p-dioxanone, polytrimethylene malonate-poly-dioxanone, and others; 4. Polyanhydrides such as polysebacic anhydride, copolyanhydrides of sebacic acid and 1,3-propane-bis-(4-oxybenzoate), poly(sebacic acide-co-bis-(p-carboxyphenoxy)propane), and others; 5. Polyorthoesters; 6. Aminoacide derived polymer such as polypeptides, amino acid salts of polyester polymers listed in No. 1 above; 7. Polyester-amides such as polymorpholinedione, polyhexamthyleneoxamate, polyiminocarbonates, and others; 8. Polyphosphazenes; 9. alkoxy-alkyl cyanoacrylates and polyoxalates as modifiers.

Naturally derived polymers and their derivatives: 1. Proteins such as Albumin, Collagen, Gelatin, Fibrin, Laminin, Elastin, Isolated Soy Protein, acylated Ispolated Soy Protein, acylated insulin, acylated Epidermal Growth factor, Glycoproteins, and others; 2. Polysaccharides such as Chitosan, Alginates, Hyaluronic Acid, acylated Chitosan, Amylose, and others; 3. Biosynthetic Polyesters, such as 3-hydroxybutyrate polymers, bacterial polyesters, poly(3-hydroxybutyrate-co-3-hydroxyvalerate), other polyhydroxyalkanoates, and other; 4. Glycosamineoglycans, such as poly(chonroitin-4-sulfate), poly(chondroitin-6-suflate), poly(heparan sulfate), Heparan, Hyalouronate, Keratan sulfacte, and other.

Preferred biodegradable polymers include polylactide, and poly(lactide-glycolide) with different lactide to glycolide ratios and different molecular weights.

The selection of the polymer solvent generally depends on the polymer and the active agent chosen, as well as the particular method of solvent removal to be employed. Organic compounds useful as solvents in dissolving the synthetic polymers described above are to be found in the following classes. Hydrocarbon: Aliphatic, cycloaliphatic, paraffinic, isoparrafinic, alicyclic, aromatic or arenes, and alkenes such as hexane, dodecane, cycloheptane, cyclooctane, methylcyclopentane, dimethylcyclopentane, isooctane, cyclobutylhexane, benzene, ethylbenzene, toluene, xylene, trimethylbenzene, and other similar compounds. Alcohol: Primarily alcohols such as ethanol, propanol, butyanol, benyzyl alcohol, allyl alcohol, ethylene glycol, and others; secondary alcohols such as 2-methyl-2-pentanol, cyclohexanediol, isobutanol, and others; tertiary alcohols such as 2-methyl-2-pentanol, nonafluro-2-methyl-2-propanol, and other similar compounds. Alkyl Halides: Dicholoromethane, chloroform, dichloroethylene, dicholoroethane, ethyl bromide, 2-bromobutane, dichloromethylhexane, tetrachloroethane, tetrachloroetylene, and other liquid alkyl halides. Aromatic Halides: Chlorobenzene, dicholorobenzene, bromobenzene, and other liquid aromatic halides. Nitroparaffins, nitroolefins, nitroalcohols, nitroketones: Nitromethane, nitroethane, nitropropane, nitrobutane, nitrobutanol, nitrocyclohexane, nitrocyclohexene, nitrocyclohexanone, and other similar compounds. Ethers: Diethyl ether, methyl ethyl ether, diisopropyl ether, tetrrahydrofuran, anisole, crown ethers, dimethoxybenzene, glyme, diglyme, butoxyethanol, methoxpropanol, propoxybutanol, ethyl vinyl ether, and other similar compounds. Aldehydes and Ketones: Acetone, Methyethyl ketone, methylisobutyl ketone, diisobutyl ketone, diacetone alcohol, isophorone, pentanal, cyclohexanone, pentanone, 4-hexene-2-one, 2,4-hexandedione, 3-hexanone, 3-methylbutanal, 4-chloro-2-penatonone, and other similar compounds. Esthers: Ethyl acetate, butyl acetatel, methyl butanoate, isopentyl acetate, methyl benzoate, ethyl-2-pentenoate, and similar compounds. Amides and Nitriles: Formamide, dimethyl formamide, dimethyl acetamide, methyl cyanide, benzonitrile, acetonitrile, bromoacetonitrile, hexanedinitrile, hexenedinitrile, and similar compounds. Suffoxides and Sulfones: Dimethyl sufloxide, dimethyl sulfone, and other similar compounds. Other useful solvents: Water, water-based salt and buffer solutions such as saline, phosphate buffered saline, and others, water solutions adjusted with acid or base, water solutions containing surface active materials such as Tween, Span, and other non-ionic and/or ionic surfactants, water solutions containing colloids such as modified cellulosics like CMC, Methylcellulose, and others, polyvinylalcohols, gums and polysaccharides such as guar, Kelzan, and others. Organic solvents such as dichlorethane, trichlorethane, xylenes or any combination of them are preferred for use PLLA or PLGA. The amount of the polymer used is selected to provide a polymer solution viscosity suitable for jetting and or forming an emulsion. The amount of polymer in the polymer-solvent mixture should be lower than, for example 50% (w:v), preferably 8% (w:v), and more preferably 3% (w:v).

After the polymer is completely dissolved in the solvent, the active ingredient is mixed with polymer solution 12 using mixing methods well known in the art.

Essentially any substance, or agent, can be encapsulated using the present method. The substance preferably is an active agent. As used herein, the terms "active agent" refers to an agent which possesses therapeutic, prophylactic, or diagnostic properties in vivo, for example when administered to an animal, including mammals, such as humans. Examples of suitable therapeutic and/or prophylactic active agents include proteins, such as hormones, antigens, and growth factors; nucleic acids, such as antisense molecules; and smaller molecules, such as antibiotics, steroids, decongestants, neuroactive agents, anesthetics, and sedatives. Examples of suitable diagnostic and/or therapeutic active agents include radioactive isostopes and radioopaque agents.

The active agent can include organic molecules such as a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, vitamin, including vitamin C and vitamin E, or combination thereof.

Representative therapeutic active agents include immunosuppressants, antioxidants, anesthetics, chemotherapeutic agents, steroids, (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers. Other non-limiting examples of active agents include anti-infectives such as nitrofurazone, sodium propionate, antibiotics, including penicillin, tetracycline, oxytetracycline, chlorotetracyclilne, bacitracin, nystatin, streptomycin, neomycin, polymyxin, gramicidin, chloramphenicol, erythromycin, and azithromycin; sulfonamides, including sulfacetamide, sulfamethoizole, sulfamethazine, sulfadiazine, sulfamerazine, and suflisoxazole, and anit-virals including ixoduridine; antiallergenics such as antazoline, methapyritene, chlorpheniramine, pyrilamine, prophyenpyridamine, hydrocortisone, cortisone, hydrocortisone acetate, dexamethosone, dexamethasone 21-phosphase, fluocinolone, traimcinolone, medrysone, prednisolone, prednisolone 21-sodium succinate, and prednisolone acetate, desensitizing agents such as ragweed pollen antigens, hay fever pollen antigens, dust antigen and milk antigen; decongestants such as phyenylephrine, naphoazoline, and tetrahydrazoline; miotics and anticholinesterases such as pilocarpine, esperine salicylate, carbachol, diisopropyle flurophosphate, phospholine iodide, and demecarium, bromide; parasympatholytics such as atropine sulfate, cyclopentolate, homatropine, scopolamine, tropicamide, eucatrpine, and hydroxyamphetamine; sympathomimetics such as epinephrine; sedatives and hynotics such a pentobarbital sodium, pheonbarbital, secobarbital sodium, codeine, (a-bromoisovaleryl) urea, carbromal; psychic energizers such as 3-(2-aminopropyl) indole acetate and 3-(2-aminobutyl) indole acetate; tranquilizers such as reserpine, chlororomayline, and thiopropazate; androgenic steroids such as methyl-testosterone and fluorymesterone; estrogens such as estone, 17-.beta.-estradiol, ethinyl estradiol, and diethyl stilbestrol; progestational agents such as progesterone, megestrol, melengestrol, chloromadionone, ethisterone, norethynodrel, 19-norporgesterone, norethindrone, medroxyprogesterone and 17-.beta.-hydroxy-progesterone; humoral agents such as the prostaglandins, for example PGE.sub.1, PGE.sub.2 and PGF.sub.2; antipyretics such as aspirin, sodium salicylate, and salicylamide; antispasmodics such as atropine, methantheline, papaverine, and methscopolamine bromde; antimalarials such as the 4-aminoquinonles, 8-aminoquinolines; chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; nutritional agents such as vitamins, natural and synthetic bioactive peptides and proteins, including growth factors, cell adhesion factors, cytokines, and biological response modifiers.

The preferred active agents are cytotoxics, preferably paclitaxel. Agents such as insecticides, pesticides, fungicides, rodenticides, plant nutrients and growth promoters can also be encapsulated. Tissue, tissue extracts and living cells can also be encapsulated. The present method can be used to encapsulate more than one active agent. The active agent also can be mixed with one or more excipients, such as stabilizing agents, known in the art. The amount of active agent to be encapsulated and the amount used in the process will vary depending upon the particular active agent, the desired effect of the active agent at the planned release levels, and the time span over which the agent should be released.

The mixture polymer solution-active ingredient solution 12 is filtered using filters of average pore sizes lower than 10 $\mu$m, preferably 5 $\mu$m. Alternatively, no filtering is needed when the printhead 16 includes a filter. The filtered mixture is loaded in the jetting reservoir 14 and jetted in the extraction media 26.

The extraction media 26 is chosen to be a solvent for the continuous phase components and the dispersed phase solvent and a nonsolvent for the excipients. When water insoluble excipients are used, the extraction media 26 preferably is deionized water. The extraction media 26 may contain buffers to limit active agent solubility in the extraction phase.

Any of the common buffers, such as phosphate, acetate, or tris, are suitable, provided that they are compatible with the sufactant system chosen. When making microparticles for pharmaceutical or biomedical applications, the buffer also should be pharmaceutically acceptable. The buffering system should be selected to provide a pH at which the active ingredient is minimally soluble. If the active ingredient is paclitaxel, the preferred buffer is PBS with a pH of 7.4.

Other suitable extraction media 26 can be used depending on the specific polymer/drug/emulsifier system being used. For example, water-soluble organic solvents that are nonsolvents for the excipient can be used as a component of the extraction phase to increase the capacity of the extraction phase to extract the dispersed phase solvent. Examples that are useful for PLGAs include alcohols, particularly poly (hydric alcohols) such as glycerol. When water is used as the dispersed phase solvent, extraction phase solvents such as ethyl acetate, long chain alcohols and ketones may be used alone or in combination as the extraction phase.

The continuous phase generally contains at least one emulsifying agent such as egg lecithin or soya bean lecithin, or synthetic lecithins such as saturated synthetic lecithins, for example, dimyristoly phosphatidyl choline, dipalmitoyl phosphatidly choline or disteraoyl phosphtidyl choline, or unsaturated synthetic lecithins, such as dioleyl phosphatidyl choline or dilinoleyl phosphatidyl choline, free fatty acids, esters of fatty acids with polyoxyalkylen compounds like polyoxpropylene glycol and polyoxyethylene glycol; ethers of fatty alcohols with polyoxyalkylnene glycols; esters of fatty acids with polyoxyalkylated sorbitan; soaps; glycerolpolyalkylene stearate; glycerol-polyoxyethylene ricinoleate; homo- and co-polymers of polyalkylene glycols; polyethoxylated soya-oil and castor oil as well as hydrogenated derivatives; ethers and esters of sucrose or other carbohydrates with fatty acids, fatty alcohols, these being optionally plyoxyalkylated; mono-, di-, and tri-glycerides of saturated or nonsaturated fatty acids, glycerides or soya-oil and sucrose, natural and synthetic forms of bile salts or bile acids, both conjugated with amino acids and nonconjugated such as taurodeoxycholate, and cholic acid.

Polyvinyl alcohol is a preferred surfactant when water is used as the continuous phase solvent.

After jetting from printhead 16 is completed, the resulting microspheres 22 disposed within reservoir 24 are cured. The solvent 26 is removed (evaporated) by continuous stirring, at low stirring speeds, preferably below 650 rpm, and more preferably at 150 rpm. Stirring should last for a least 1 hour, preferably for 1 hour and 30 minutes. The microspheres 22 are collected by centrifugation at 1,500 rpm for 5 minutes and gradually frozen in liquid nitrogen preferably for 3 hours, and more preferably for 6 hours. The microspheres 22 are dried, such as by lyophilization. Acceptable techniques to lyophilize the mixture include those known in the art.

The final microspheres 22 are in the form of free-flowing powder that is easily injected. Typically, the microspheres will be of a size suitable for injection. A preferred size range for the microspheres is approximately 1 to 180 μm in diameter.

Other alteration and modification of the invention will likewise become apparent to those of ordinary skill in the art upon reading the present disclosure, and it is intended that the scope of the invention disclosed herein be limited only by the broadest interpretation of the appended claims to which the inventor is legally entitled.

I claim:

1. A method for forming polymer microspheres comprising:

dispensing polymeric material from an orifice of an ink-jet printhead while the orifice is immersed in a liquid.

2. The method of claim 1 wherein the ink-jet printhead is a drop-on-demand printhead.

3. A method for forming polymer microspheres comprising:

dispensing polymeric material from an orifice of a drop-on-demand ink-jet printhead while the orifice is immersed in a solvent extraction media.

4. The method of claim 3 wherein the ink-jet printhead includes a piezoelectric device.

5. A method for forming polymer microspheres comprising:

forming a solution of a biodegradable polymer, a solvent and an active agent;

dispensing the solution from an orifice of a drop-on-demand ink-jet printhead to form spheres while the orifice is immersed in a solvent extraction media;

extracting the solvent from the spheres; and collecting the spheres.

* * * * *